US012392846B2

(12) United States Patent
Taracila et al.

(10) Patent No.: US 12,392,846 B2
(45) Date of Patent: Aug. 19, 2025

(54) FLEXIBLE IN BORE RECEIVING COIL ARRAY FOR A MAGNETIC RESONANCE IMAGING SYSTEM

(71) Applicant: GE Precision Healthcare LLC, Wauwatosa, WI (US)

(72) Inventors: Victor Taracila, Orange Village, OH (US); Ravi Shankar Jaiswal, Florence, SC (US); Victoria Poli Zemskov, Twinsburg, OH (US); Fraser John Laing Robb, Aurora, OH (US); Emily Rose Long, Milwaukee, WI (US); Jana Michelle Vincent, Aurora, OH (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 302 days.

(21) Appl. No.: 18/124,825

(22) Filed: Mar. 22, 2023

(65) Prior Publication Data

US 2024/0319298 A1 Sep. 26, 2024

(51) Int. Cl.
*G01R 33/34* (2006.01)
*A61B 5/00* (2006.01)
*A61B 5/055* (2006.01)
*G01R 33/3415* (2006.01)

(52) U.S. Cl.
CPC ........ *G01R 33/34084* (2013.01); *A61B 5/055* (2013.01); *A61B 5/704* (2013.01); *G01R 33/3415* (2013.01)

(58) Field of Classification Search
CPC .......... G01R 33/34084; G01R 33/3415; G01R 33/48; G01R 33/34; A61B 5/055; A61B 5/704
See application file for complete search history.

(56) References Cited

U.S. PATENT DOCUMENTS

| 7,446,531 | B2 | 11/2008 | Schnell et al. | |
| 7,602,186 | B2 * | 10/2009 | Hoogeveen | G01R 33/341 324/309 |
| 9,250,305 | B2 | 2/2016 | Bulumulla et al. | |
| 9,453,894 | B2 | 9/2016 | Bulumulla et al. | |
| 2008/0015430 | A1 * | 1/2008 | Takamori | G01R 33/3415 600/415 |
| 2008/0211495 | A1 * | 9/2008 | Steckner | G01R 33/3415 343/741 |
| 2015/0168511 | A1 * | 6/2015 | Jeong | G01R 33/3415 324/321 |
| 2024/0004007 | A1 * | 1/2024 | Berendt | A61B 5/6824 |

* cited by examiner

*Primary Examiner* — Baisakhi Roy
(74) *Attorney, Agent, or Firm* — Fletcher Yoder, P.C.

(57) ABSTRACT

An MRI system includes an MRI scanner having a bore and a table configured to move a subject to be imaged into and out of the bore. The MRI system includes a flexible RF receiving coil array integrated within the bore and electronically coupled directly to the MRI scanner, wherein the flexible RF receiving coil array remains in the bore regardless of a position of the table, and the flexible RF receiving coil array is located underneath the table when the table is located within the bore. The MRI system includes an automated mechanism configured to automatically move the flexible RF receiving coil array from underneath the table on a first side of the subject, to pull the flexible RF receiving coil array over the subject from the first side to a second side of the subject, and to fasten the flexible RF receiving coil on the second side.

20 Claims, 15 Drawing Sheets

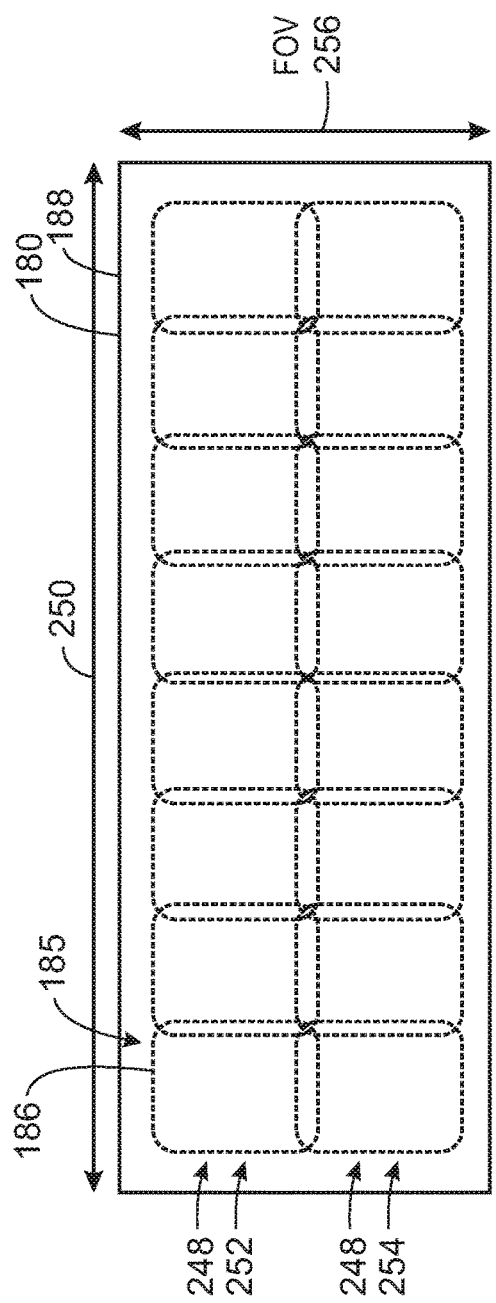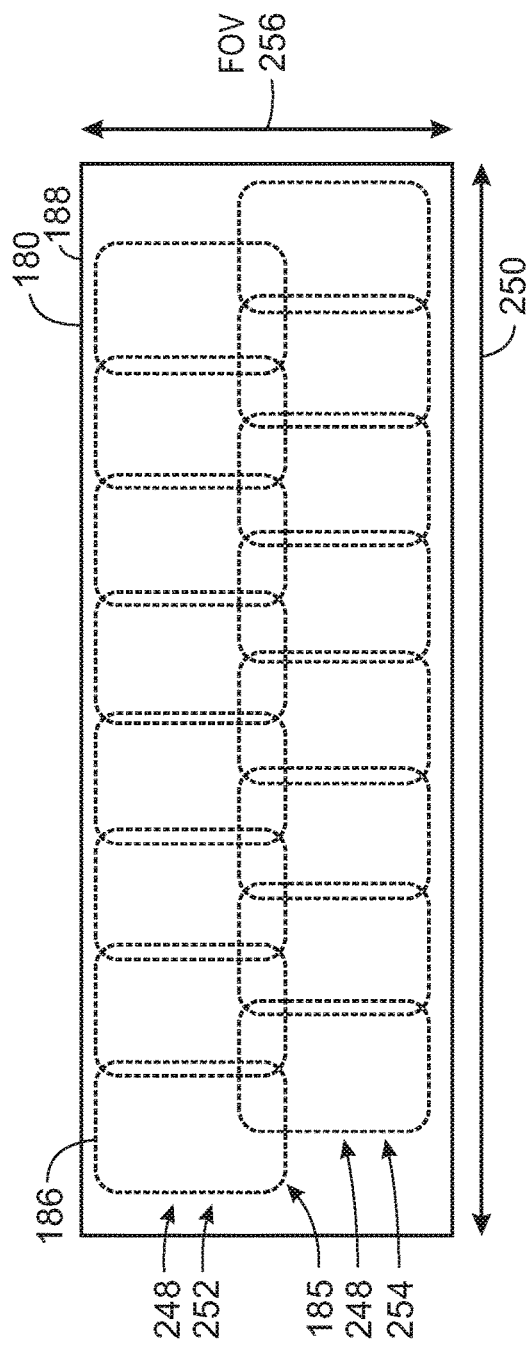

FLEXIBLE IN BORE RECEIVING COIL ARRAY FOR A MAGNETIC RESONANCE IMAGING SYSTEM

BACKGROUND

The subject matter disclosed herein relates to medical imaging and, more particularly, to a flexible in bore receiving coil array for a magnetic resonance imaging (MRI) system.

Non-invasive imaging technologies allow images of the internal structures or features of a patient/object to be obtained without performing an invasive procedure on the patient/object. In particular, such non-invasive imaging technologies rely on various physical principles (such as the differential transmission of X-rays through a target volume, the reflection of acoustic waves within the volume, the paramagnetic properties of different tissues and materials within the volume, the breakdown of targeted radionuclides within the body, and so forth) to acquire data and to construct images or otherwise represent the observed internal features of the patient/object.

During MRI, when a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, or "longitudinal magnetization", $M_z$, may be rotated, or "tipped", into the x-y plane to produce a net transverse magnetic moment, $M_t$. A signal is emitted by the excited spins after the excitation signal $B_1$ is terminated and this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradient fields vary according to the particular localization method being used. The resulting set of received nuclear magnetic resonance (NMR) signals are digitized and processed to reconstruct the image using one of many well-known reconstruction techniques.

To enhance signal-to-noise ratio in MRI systems receiving coil arrays are utilized. One of the problems with these receiving coil arrays is their specificity. In particular, receiving coil arrays are configured to image only specific parts of the human body. The typical receiving coil arrays may be unusable in certain situations. For example, size variations in the patient or particular medical conditions may make typical receiving coil arrays unusable. Even if a receiving coil array is sufficiently flexible to be wrapped around any part of the body, it still requires a technician to assist in correctly placing it. In addition, MRI systems usually need many more receiving channels than receiving elements in the field of view which makes cabling a complex problem.

SUMMARY

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In one embodiment, a magnetic resonance imaging (MRI) system is provided. The MRI system includes an MRI scanner having a bore. The MRI system also includes a table configured to move a subject to be imaged into and out of the bore of the MRI scanner. The MRI system further includes a flexible radio frequency (RF) receiving coil array integrated within the bore and electronically coupled directly to the MRI scanner, wherein the flexible RF receiving coil array remains in the bore regardless of a position of the table, and the flexible RF receiving coil array is located underneath the table when the table is located within the bore. The MRI system still further includes an automated mechanism configured to automatically move the flexible RF receiving coil array from underneath the table on a first side of the subject, to pull the flexible RF receiving coil array over the subject from the first side to a second side of the subject opposite the first side, and to fasten the flexible RF receiving coil array on the second side in preparation for a scan with the MRI scanner.

In another embodiment, a method for performing a magnetic resonance imaging (MRI) scan is provided. The method includes moving a subject into a bore of an MRI scanner via a table. The method also includes utilizing an automated mechanism to automatically move a flexible radio frequency (RF) receiving coil array from underneath the table on a first side of the subject, to pull the flexible RF receiving coil array over the subject from the first side to a second side of the subject opposite the first side, and to fasten the flexible RF receiving coil array on the second side in preparation for a scan with the MRI scanner, wherein the flexible RF receiving coil array is integrated within the bore and electronically coupled directly to the MRI scanner, the flexible RF receiving coil array remains in the bore regardless of a position of the table, and the flexible RF receiving coil array is located underneath the table when the table is located within the bore.

In a further embodiment, a magnetic resonance imaging (MRI) system is provided. The MRI system includes an MRI scanner having a bore. The MRI system also includes a table configured to move a subject to be imaged into and out of the bore of the MRI scanner. The MRI system further includes a flexible radio frequency (RF) receiving coil array integrated within the bore and electronically coupled directly to the MRI scanner, wherein the flexible RF receiving coil array is configured to be completely wrapped around any anatomical portion of the subject, the flexible RF receiving coil array remains in the bore regardless of a position of the table, and the flexible RF receiving coil array is located underneath the table when the table is located within the bore. The MRI system still further includes an automated mechanism configured to automatically move the flexible RF receiving coil array from underneath the table on a first side of the subject, to pull the flexible RF receiving coil array over the subject from the first side to a second side of the subject opposite the first side, and to fasten the flexible RF receiving coil array on the second side in preparation for a scan with the MRI scanner. The flexible RF receiving coil array includes a plurality of channels, each channel of the plurality of channels is located within a field of view of the MRI scanner and is utilized during the scan, and the plurality of channels are arranged in a plurality of rows along a longitudinal length of the flexible RF receiving coil array.

BRIEF DESCRIPTION OF THE DRAWINGS

These and other features, aspects, and advantages of the present subject matter will become better understood when the following detailed description is read with reference to the accompanying drawings in which like characters represent like parts throughout the drawings, wherein:

FIG. 9 illustrates a linear arrangement of channels of a flexible RF receiving coil array, in accordance with aspects of the present disclosure;

FIG. 10 illustrates a staggered arrangement of channels of a flexible RF receiving coil array, in accordance with aspects of the present disclosure;

DETAILED DESCRIPTION

Figure 1:
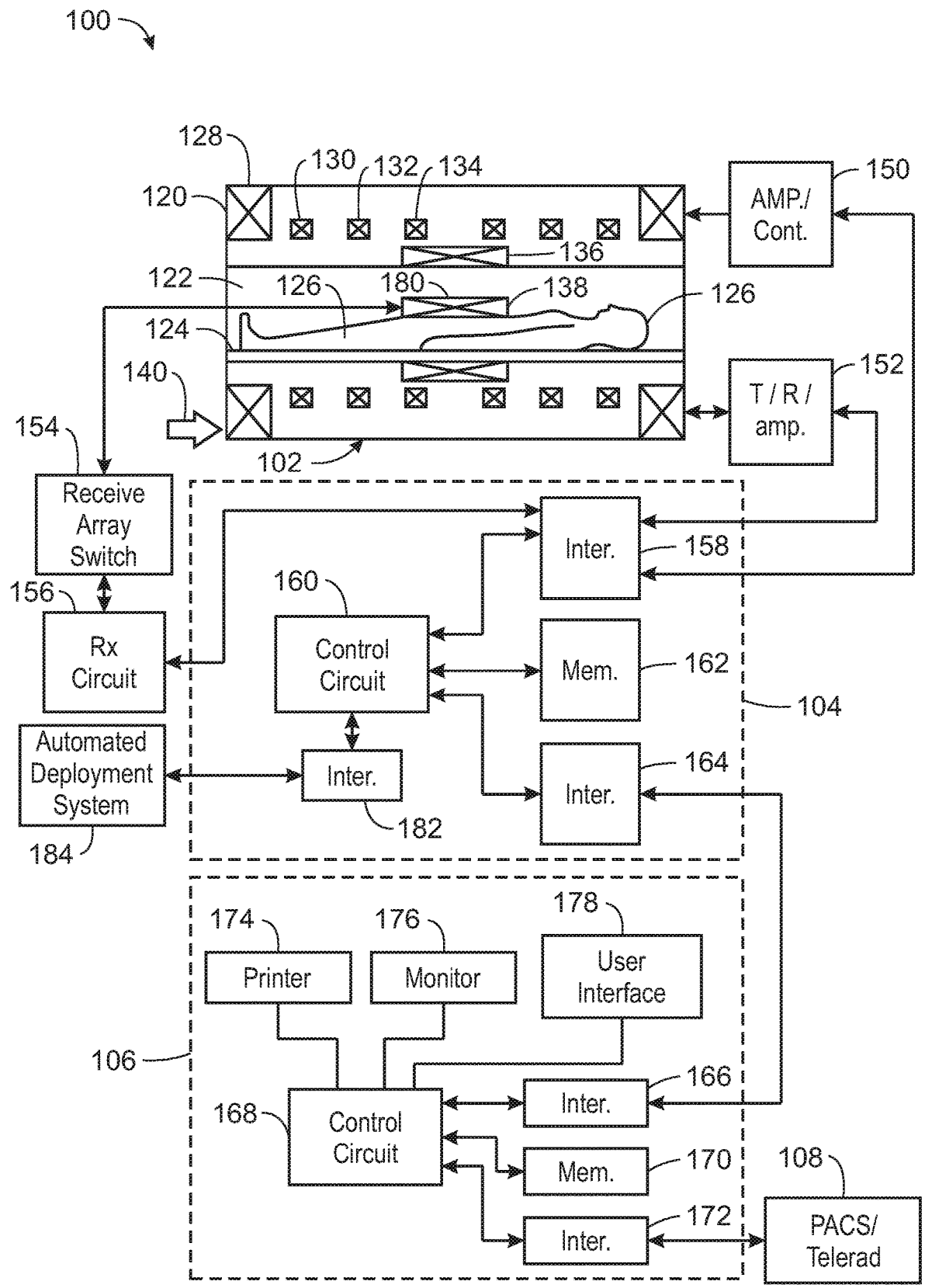
FIG. 1 illustrates an embodiment of a magnetic resonance imaging (MRI) system, in accordance with aspects of the present disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While aspects of the following discussion are provided in the context of medical imaging, it should be appreciated that the disclosed techniques are not limited to such medical contexts. Indeed, the provision of examples and explanations in such a medical context is only to facilitate explanation by providing instances of real-world implementations and applications. However, the disclosed techniques may also be utilized in other contexts, such as image reconstruction for non-destructive inspection of manufactured parts or goods (i.e., quality control or quality review applications), and/or the non-invasive inspection of packages, boxes, luggage, and so forth (i.e., security or screening applications). In general, the disclosed techniques may be useful in any imaging or screening context or image processing or photography field where a set or type of acquired data undergoes a reconstruction process to generate an image or volume.

The present disclosure provides systems and methods for a flexible in bore receiving coil array for MRI system. In particular, a flexible radio frequency (RF) receiving coil array (e.g., body coil array) is integrated within (e.g., disposed within and permanently coupled to) a bore of an MRI scanner. The flexible RF receiving coil array is electronically coupled directly to the MRI scanner (via a single connection). The flexible RF receiving coil array remains in the bore regardless of the position of a table that moves a subject (e.g., patient or object) into and out of the bore. In particular, the flexible RF receiving coil array is not coupled to the table (regardless of the position of the table). The flexible RF receiving coil array is located underneath the table when the table is located within the bore. The flexible RF receiving coil array is configured to be wrapped around any anatomical portion (e.g., head, torso, pelvis, and legs) of the subject to be imaged. A longitudinal length of the flexible RF receiving coil array is at least equal to a circumference of a largest subject that can be scanned within the bore of the MRI scanner.

The flexible RF receiving coil array includes a plurality channels, where each channel is located within a field of view of the MRI scanner and is utilized during the scan. The plurality of channels is arranged in a plurality of rows (e.g., 2 or more rows) along a longitudinal length of the flexible RF receiving coil array. In certain embodiments, the plurality of rows is aligned along a field of view. In certain embodiments, the plurality of channels is staggered with respect to each other along the longitudinal length (or longitudinal axis) of the flexible RF receiving coil array.

An automated mechanism is configured to automatically move the flexible RF receiving coil array from underneath the table on a first side of the subject, to pull the flexible RF receiving coil array over the subject from the first side to a second side of the subject opposite the first side, and to fasten the flexible RF receiving coil array on the second side in preparation for a scan within the MRI scanner (e.g., similar to how a seatbelt is secured). The automated mechanism is configured, after the scan of the subject, to automatically uncoupled the flexible RF receiving coil array and to return the flexible RF receiving coil array to underneath the table. In certain embodiments, after the initial scan, the table (and the subject) may be moved relative to the bore to reposition the subject and the process for deploying and securing the flexible RF receiving coil array is repeated in preparation for a second scan (e.g., of a different portion of the anatomy of the subject). In certain embodiments, the automated mechanism includes a tension spring (e.g., pull spring) that upon release or unfastening of the flexible RF receiving coil array from the second side returns the flexible RF receiving coil array to underneath the table. In certain embodiments, the automated mechanism includes a curved arm coupled to a drive mechanism, wherein the curved arm is configured to couple to the flexible RF receiving coil array, and the drive mechanism is configured to rotate the curved arm to pull the flexible RF receiving coil array about the subject. In certain embodiments, a set of rollers to keep an excess portion of the flexible RF receiving coil array not disposed over the subject during the scan in a rolled or folded arrangement underneath the table.

The disclosed embodiments eliminate the need for any connectors or cables for use with RF receiving coils in the table utilized for an MRI scan. Thus, the table can be utilized purely as a mechanical support. The disclosed embodiments also eliminate the need for coil placement and adjustment by a medical technician. The disclosed embodiments further enable all existing channels to be in the field of view and to be utilized during a scan. The disclosed embodiments provide for a flexible RF receiving coil array that can be utilized for scanning all parts of the anatomy. This may increase or speed up workflow. This may also reduce costs associated with medial professional assistance. This may also reduce costs since a scanner does not need to be equipped with multiple types of RF receiving coils.

With the preceding in mind, FIG. 1 a magnetic resonance imaging (MRI) system 100 is illustrated schematically as including a scanner 102, scanner control circuitry 104, and system control circuitry 106. According to the embodiments described herein, the MRI system 100 is generally configured to perform MR imaging.

System 100 additionally includes remote access and storage systems or devices such as picture archiving and communication systems (PACS) 108, or other devices such as teleradiology equipment so that data acquired by the system 100 may be accessed on- or off-site. In this way, MR data may be acquired, followed by on- or off-site processing and evaluation. While the MRI system 100 may include any suitable scanner or detector, in the illustrated embodiment, the system 100 includes a full body scanner 102 having a housing 120 through which a bore 122 is formed. A table 124 is moveable into the bore 122 to permit a patient 126 (e.g., subject) to be positioned therein for imaging selected anatomy within the patient.

Scanner 102 includes a series of associated coils for producing controlled magnetic fields for exciting the gyromagnetic material within the anatomy of the patient being imaged. Specifically, a primary magnet coil 128 is provided for generating a primary magnetic field, $B_0$, which is generally aligned with the bore 122. A series of gradient coils 130, 132, and 134 permit controlled magnetic gradient fields to be generated for positional encoding of certain gyromagnetic nuclei within the patient 126 during examination sequences. A radio frequency (RF) coil 136 (e.g., RF transmit coil) is configured to generate radio frequency pulses for exciting the certain gyromagnetic nuclei within the patient. In addition to the coils that may be local to the scanner 102, the system 100 also includes a set of receiving coils or RF receiving coils 138 (e.g., an array of coils) configured for placement proximal (e.g., against) to the patient 126. As an example, the receiving coils 138 can include cervical/thoracic/lumbar (CTL) coils, head coils, single-sided spine coils, and so forth. Generally, the receiving coils 138 are placed close to or on top of the patient 126 so as to receive the weak RF signals (weak relative to the transmitted pulses generated by the scanner coils) that are generated by certain gyromagnetic nuclei within the patient 126 as they return to their relaxed state.

The various coils of system 100 are controlled by external circuitry to generate the desired field and pulses, and to read emissions from the gyromagnetic material in a controlled manner. In the illustrated embodiment, a main power supply 140 provides power to the primary field coil 128 to generate the primary magnetic field, Bo. A power input (e.g., power from a utility or grid), a power distribution unit (PDU), a power supply (PS), and a driver circuit 150 may together provide power to pulse the gradient field coils 130, 132, and 134. The driver circuit 150 may include amplification and control circuitry for supplying current to the coils as defined by digitized pulse sequences output by the scanner control circuitry 104.

Another control circuit 152 is provided for regulating operation of the RF coil 136. Circuit 152 includes a switching device for alternating between the active and inactive modes of operation, wherein the RF coil 136 transmits and does not transmit signals, respectively. Circuit 152 also includes amplification circuitry configured to generate the RF pulses. Similarly, the receiving coils 138 are connected to switch 154, which is capable of switching the receiving coils 138 between receiving and non-receiving modes. Thus, the receiving coils 138 resonate with the RF signals produced by relaxing gyromagnetic nuclei from within the patient 126 while in the receiving mode, and they do not resonate with RF energy from the transmitting coils (i.e., coil 136) so as to prevent undesirable operation while in the non-receiving mode. Additionally, a receiving circuit 156 is configured to receive the data detected by the receiving coils 138 and may include one or more multiplexing and/or amplification circuits.

The receiving coil 138 utilized is a flexible RF receiving coil array 180 that is integrated within the bore 122 of the MRI scanner 102. The flexible RF receiving coil array 180 is electronically coupled directly to the MRI scanner 102 (via a single connection). The flexible RF receiving coil array 180 remains in the bore 122 regardless of the position of the table 124 that moves the patient 126 into and out of the bore 122. In particular, the flexible RF receiving coil array 180 is not coupled to the table 124 (regardless of the position of the table 124). As discussed herein, the flexible RF receiving coil array 180 is located underneath the table 124 (e.g., in a stored position) when the table 124 is located within the bore 122. In certain embodiments, the flexible RF receiving coil array 180 is located above the table 124 in a stored position. The flexible RF receiving coil array 180 is configured to be wrapped around any anatomical portion (e.g., head, torso, pelvis, and legs) of the patient 126 to be imaged. A longitudinal length of the flexible RF receiving coil array 180 is at least equal to a circumference of a largest patient 126 that can be scanned within the bore 122 of the MRI scanner 102.

It should be noted that while the scanner 102 and the control/amplification circuitry described above are illustrated as being coupled by a single line, many such lines may be present in an actual instantiation. For example, separate lines may be used for control, data communication, power transmission, and so on. Further, suitable hardware may be disposed along each type of line for the proper handling of the data and current/voltage. Indeed, various filters, digitizers, and processors may be disposed between the scanner and either or both of the scanner and system control circuitry 104, 106.

As illustrated, scanner control circuitry 104 includes an interface circuit 158, which outputs signals for driving the gradient field coils and the RF coil and for receiving the data representative of the magnetic resonance signals produced in examination sequences. The interface circuit 158 is coupled to a control and analysis circuit 160. The control and analysis circuit 160 executes the commands for driving the circuit 150 and circuit 152 based on defined protocols selected via system control circuit 106.

Control and analysis circuit 160 also serves to receive the magnetic resonance signals and performs subsequent processing before transmitting the data to system control circuit 106. Scanner control circuit 104 also includes one or more memory circuits 162, which store configuration parameters, pulse sequence descriptions, examination results, and so forth, during operation.

Interface circuit 164 is coupled to the control and analysis circuit 160 for exchanging data between scanner control circuitry 104 and system control circuitry 106. In certain embodiments, the control and analysis circuit 160, while illustrated as a single unit, may include one or more hardware devices. The system control circuit 106 includes an interface circuit 166, which receives data from the scanner control circuitry 104 and transmits data and commands back to the scanner control circuitry 104. The control and analysis circuit 168 may include a CPU in a multi-purpose or application specific computer or workstation. Control and analysis circuit 168 is coupled to a memory circuit 170 to store programming code for operation of the MRI system 100 and to store the processed image data for later reconstruction, display and transmission. The programming code may execute one or more algorithms that, when executed by a processor, are configured to perform reconstruction of acquired data as described below. In certain embodiments, image reconstruction may occur on a separate computing device having processing circuitry and memory circuitry.

An additional interface circuit 172 may be provided for exchanging image data, configuration parameters, and so forth with external system components such as remote access and storage devices 108. Finally, the system control and analysis circuit 168 may be communicatively coupled to various peripheral devices for facilitating operator interface and for producing hard copies of the reconstructed images. In the illustrated embodiment, these peripherals include a printer 174, a monitor 176, and user interface 178 including devices such as a keyboard, a mouse, a touchscreen (e.g., integrated with the monitor 176), and so forth.

A further interface circuit 182 may be provided to couple to an automated deployment system 184. The automated deployment system 184 is configured to automatically (without any assistance from an operator) deploy (from a stored position) and secure the flexible RF receiving coil array 180 integrated within the bore 122 about the patient 126 (in a deployed position) in preparation for a scan. In the deployed position, the flexible RF receiving coil array 180 is disposed about (e.g., wrapped about) the contours of the patient in a region to be imaged. The automated deployment system 184 is also configured to automatically return the flexible RF receiving coil array 180 to its stored position. The automated deployment system 184 may include an automated mechanism for the movement of the flexible RF receiving coil array 180 between a stored position and a deployed position. The control circuit 160 may provide control signals for the actuation of the automated deployment system 184.

Figure 2:
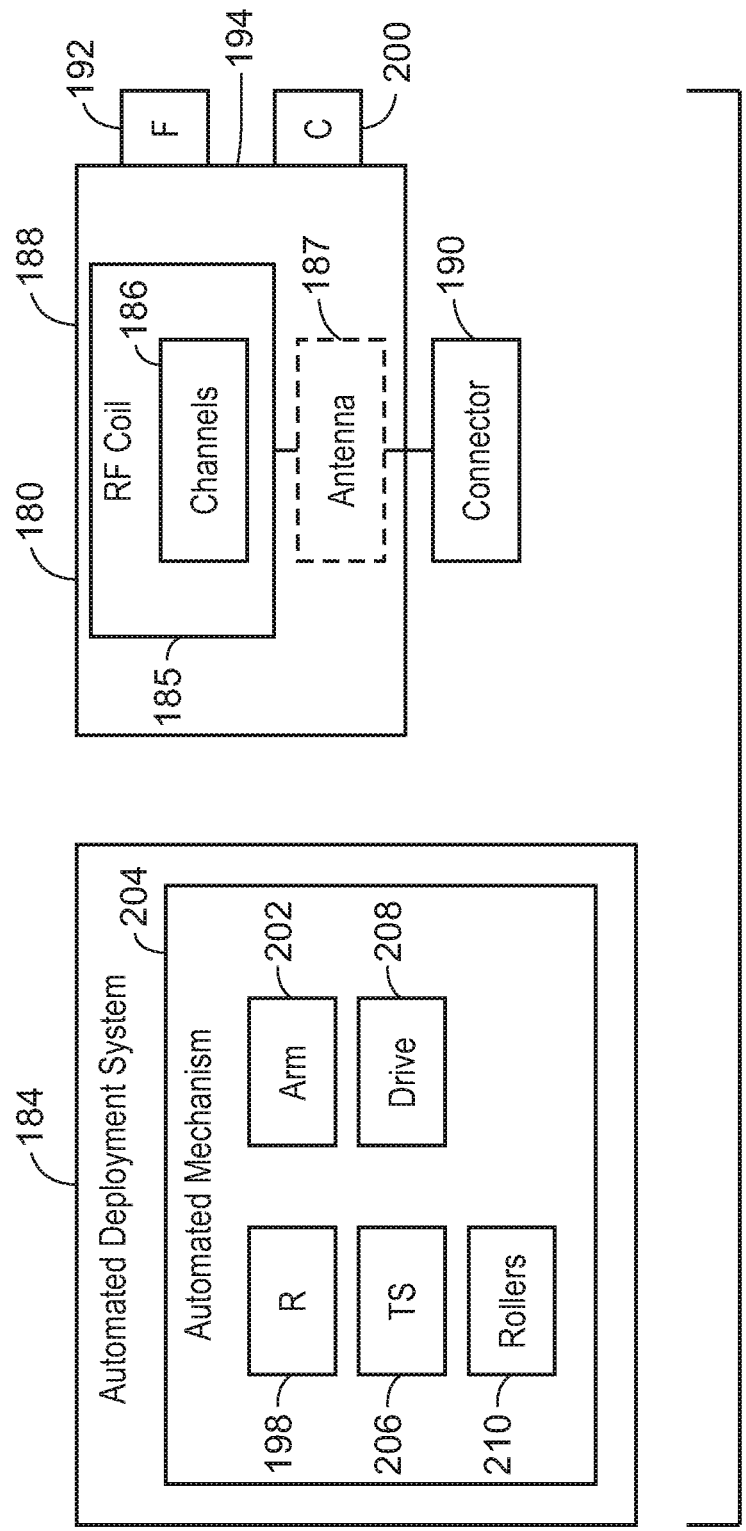
FIG. 2 illustrates a flexible RF receiving coil array and an automated deployment system for manipulating the flexible RF receiving coil array, in accordance with aspects of the present disclosure.

FIG. 2 illustrates the flexible RF receiving coil array 180 and the automated deployment system 184 for manipulating the flexible RF receiving coil array 180. The flexible RF receiving coil array 180 includes an RF coil 185 having a plurality of channels 186 (e.g., elements or loops) disposed within a flexible enclosure 188. Each channel 186 is located within a field of view and is utilized during the scan. The plurality of channels 186 is arranged in a plurality of rows (e.g., 2 or more rows) along a longitudinal length of the flexible RF receiving coil array 180. In certain embodiments, the plurality of rows is aligned along the field of view. In certain embodiments, the plurality of channels 186 is staggered with respect to each other along a longitudinal length (or a longitudinal axis) of the flexible RF receiving coil array 180. In certain embodiments, the flexible RF receiving coil array 180 is configured to wirelessly receive communication signals from the control circuitry of the MRI scanner and to wirelessly transmit scan data to the control circuitry of the MRI scanner. In certain embodiments, the flexible RF receiving coil array 180 includes an antenna 187 coupled to the RF coil 185 and configured to wirelessly receive and transmits signals. In certain embodiments, the antenna 187 may be disposed external to the flexible RF receiving coil array 180 (e.g., on an external surface of the flexible enclosure 188 or within a cradle of a table of the MRI scanner).

As noted above, the flexible RF receiving coil array 180 is integrated within (e.g., disposed within and permanently coupled to) the bore of the MRI scanner (e.g., MRI scanner 102 in FIG. 1). The flexible RF receiving coil array 180 is electronically coupled directly to the MRI scanner via single electronic connection or connector 190. The flexible RF receiving coil array 180 remains in the bore regardless of the position of a table that moves a subject (e.g., patient or object) into and out of the bore. In particular, the flexible RF receiving coil array 180 is not coupled to the table (regardless of the position of the table). The flexible RF receiving coil array 180 is located underneath the table when the table is located within the bore. The flexible RF receiving coil array 180 is configured to be wrapped around any anatomical portion (e.g., head, torso, pelvis, and legs) of the subject to be imaged. A longitudinal length of the flexible RF receiving coil array 180 is at least equal to a circumference of a largest subject that can be scanned within the bore of the MRI scanner.

In certain embodiments, the flexible RF receiving coil array 180 includes one or more fasteners 192 coupled to (or located along) a side 194 of the flexible enclosure 188. The one or more fasteners 192 are configured to fasten the flexible RF receiving coil array 180 when deployed about (e.g., wrapped around) the subject. The one or more fasteners 192 may be made of MRI-compatible material. In certain embodiments, the one or more fasteners 192 may be latches or latch plates or hooks configured to couple to or be disposed in one or more corresponding receptacles 198 (e.g., buckles) of the automated deployment system 184. The flexible RF receiving coil array 180 may also include one or more connectors 200 (e.g., hooks or receptacles) coupled to (or located along) the side 194 of the flexible enclosure 188 configured to interact with a curved arm 202 that attaches to and moves the flexible RF receiving coil array 180. The one or more connectors 200 may be made of MRI-compatible material.

The automated deployment system 184 includes an automated mechanism 204 configured to automatically move the flexible RF receiving coil array 180 from underneath the table on a first side of the subject, to pull the flexible RF receiving coil array 180 over the subject from the first side to a second side of the subject opposite the first side, and to fasten the flexible RF receiving coil array 180 on the second side in preparation for a scan within the MRI scanner (e.g., similar to how a seatbelt is secured). The automated mechanism 204 is configured, after the scan of the subject, to automatically uncoupled the flexible RF receiving coil array and to return the flexible RF receiving coil array 180 to underneath the table. Although the automated deployment system 184 is described in terms of deploying the flexible RF receiving coil array 180 from underneath the table, in certain embodiments, the automated deployment system 184 may be configured for deploying the flexible RF receiving coil array 180 from a stored position located above the table in the bore.

In certain embodiments, the automated mechanism 204 includes one or more corresponding receptacles 198 (e.g., buckles) to receive the fasteners 192 of the flexible RF receiving coil array 180 to secure the flexible RF receiving coil array 180 to the second side when deployed over (e.g., wrapped around) the subject. In certain embodiments, the corresponding receptacles 198 may release the flexible RF receiving coil array 180 (e.g., in response to a control signal provide to an actuator of the receptacles 198). In certain embodiments, the automated mechanism 204 includes a tension spring 206 (e.g., pull spring) that upon release or unfastening of the flexible RF receiving coil array 180 from the second side returns the flexible RF receiving coil array 180 to underneath the table. The tension spring 206 may also provide tension to keep flexible RF receiving coil array 180 secure (e.g., disposed along the contours) about the subject.

In certain embodiments, the automated mechanism 204 includes a curved arm 202 coupled to a drive mechanism 208 (e.g., driven by a motor) for rotating the curved arm 202 about an axis (e.g., parallel with a central axis of the bore). The curved arm 202 is configured to couple to the flexible RF receiving coil array 180, and the drive mechanism 208 is configured to rotate the curved arm 202 to pull the flexible RF receiving coil array 180 about the subject. For example, an end of the curved arm 202 may include one or more protrusions or hooks that interface with the one or more corresponding connectors on the flexible RF receiving coil array 180.

In certain embodiments, the automated mechanism 204 includes a set of rollers 210 configured to keep the flexible RF receiving coil array 180 in a rolled or folded arrangement in its stored position (e.g. beneath the table when the table is within the bore). The set of rollers 210 also are configured to keep an excess portion of the flexible RF receiving coil array 180 not disposed over the subject during the scan in the rolled or folded arrangement underneath the table.

Figure 3:
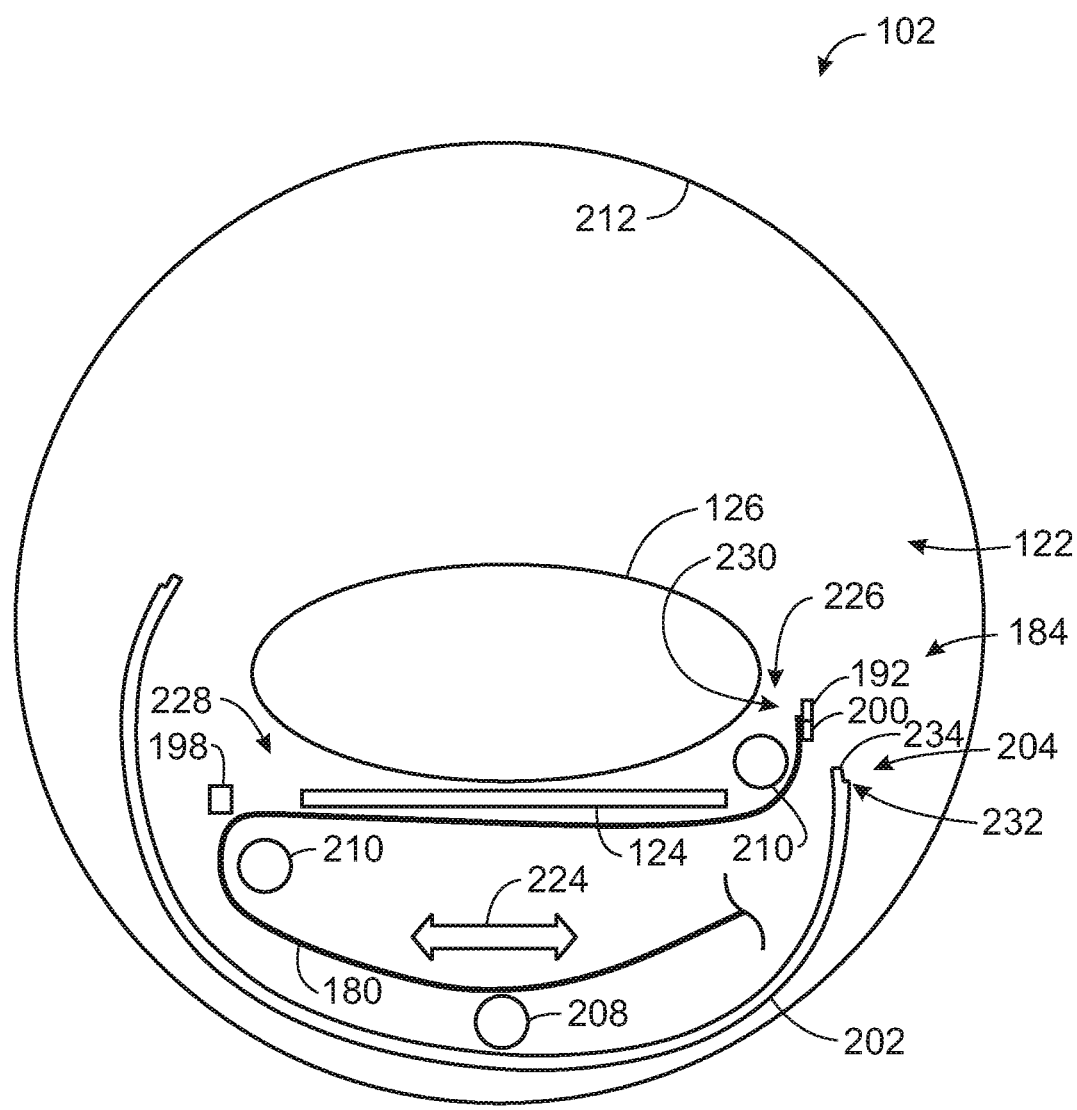
FIG. 3 illustrates a flexible RF receiving coil array prior to be disposed about a subject (e.g., in a stored position) via an automated deployment system, in accordance with aspects of the present disclosure.

FIG. 3 illustrates the flexible RF receiving coil array 180 prior to being disposed about the subject 126 (e.g., patient) via the automated deployment system 184. As depicted, the subject 126 is disposed on the table 124 within the bore 122 of the MRI scanner 102 (as defined by an inner surface 212 of the MRI scanner 102). The flexible RF receiving coil array 180 is maintained in a storage position located under the table 124 (e.g., adjacent a lower portion of the bore 122). In particular, a set of rollers 210 (as part of the automated mechanism 204) keeps the flexible RF receiving coil array 180 disposed underneath the table 124 in a rolled or folded arrangement. The flexible RF receiving coil array 180 can move back and forth along the set of rollers 210 when being deployed and returned as indicated by arrow 224.

The automated mechanism 204 is configured to automatically move the flexible RF receiving coil array 180 from underneath the table 124 on a first side 226 of the subject 126, to pull the flexible RF receiving coil array 180 over the subject 126 from the first side 226 to a second side 228 of the subject 126 opposite the first side 226, and to fasten the flexible RF receiving coil array 180 on the second side 228 in preparation for a scan within the MRI scanner 102 (e.g., similar to how a seatbelt is secured). As depicted, the automated mechanism 204 includes the curved arm 202. The curved arm 202 extends underneath the table 124 between the first side 226 and the second side 228. A portion of the curved arm 202 is also located beneath the set of rollers 210 and the flexible RF receiving coil array 180. The curved arm 202 is coupled to the drive mechanism 208 (e.g., driven by a rotor). The automated mechanism 204 includes one or more receptacles 198 located on the second side 228. An end 230 (e.g., side) of the flexible RF receiving coil array 180 may include one or more fasteners 192 for coupling the end 230 to the corresponding one or more receptacles 198 when the flexible RF receiving coil array 180 is secured (and disposed about the subject 126). The curved arm 202 is configured to couple to the flexible RF receiving coil array 180, and the drive mechanism 208 is configured to rotate the curved arm 202 to pull the flexible RF receiving coil array 180 about the subject 126. For example, an end 232 of the curved arm 202 may include one or more protrusions or hooks 234 that interface with the one or more corresponding connectors 200 (e.g., on the end 230 adjacent the one or more fasteners 192) on the flexible RF receiving coil array 180. A length (along the curve about the rotation axis) of the curved arm 202 is long enough to engage the flexible RF receiving coil on the first side 226 and to move it to the second side 228 about the subject 126. In certain embodiments, a different mechanism than the curved arm 202 may be utilized to deploy the flexible RF receiving coil array 180.

Figure 4:
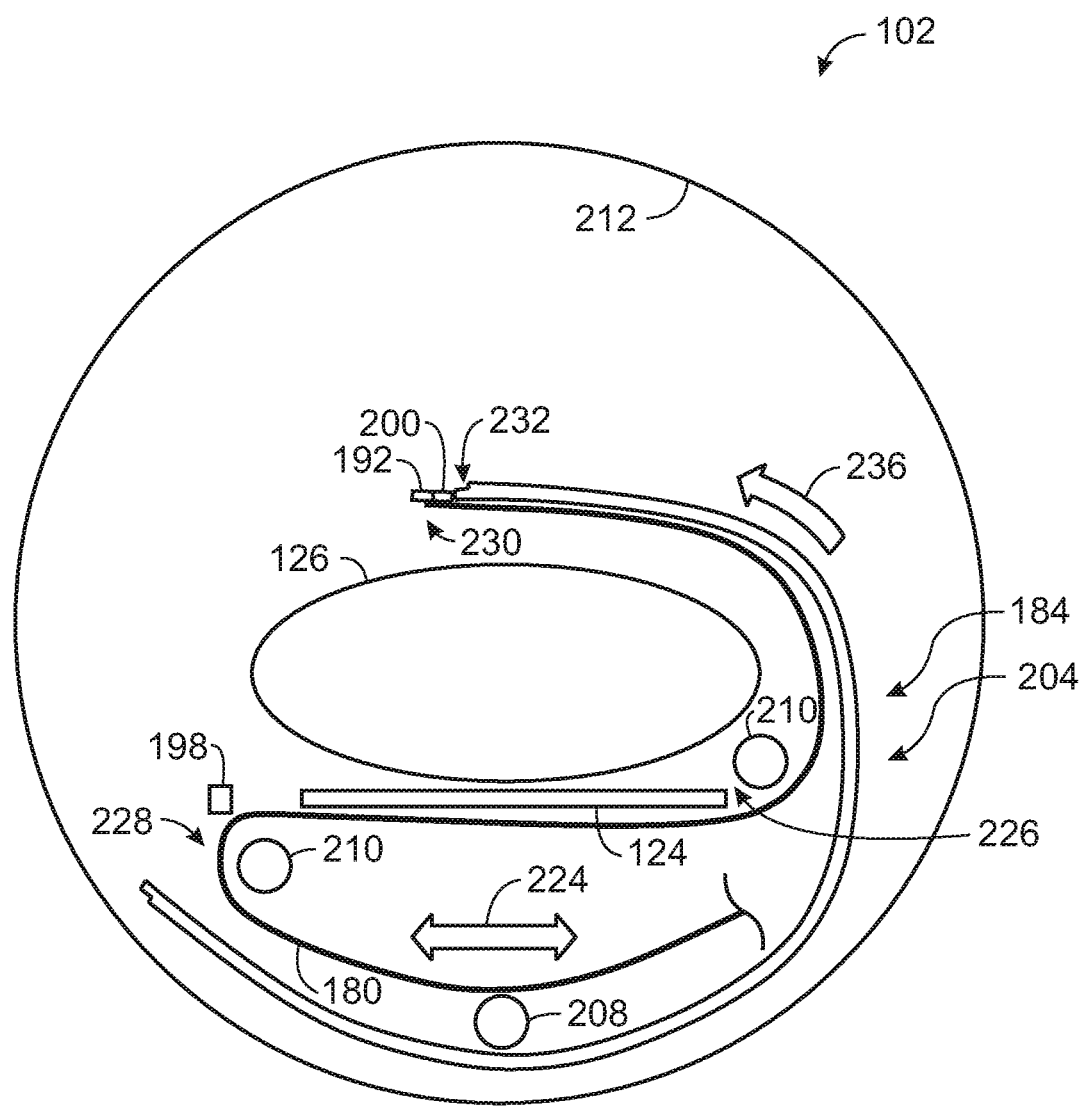
FIG. 4 illustrates the flexible RF receiving coil array in FIG. 3 being deployed about the subject utilizing the automated deployment system, in accordance with aspect of the present disclosure.

FIG. 4 illustrates the flexible RF receiving coil array 180 in FIG. 3 being deployed about the subject 126 utilizing the automated deployment system 184. The drive mechanism 208 rotates the curved arm 202 (as indicated arrow 236) so that the one or more protrusions or hooks 234 (see FIG. 3) on the end 232 of the curved arm 202 engages the one or more corresponding connectors 200 on the end 230 of the flexible RF receiving coil array 180 to couple the curved arm 202 to the flexible RF receiving coil array 180. This engagement enables the curved arm 202 to move the flexible RF receiving coil array 180 from a stored position to a deployed position (e.g., disposed about or wrapped around a portion of the subject 126). Continued rotation of the curved arm 202 by the drive mechanism 208 moves the flexible RF receiving coil array 180 from the first side 226 toward the second side 228 about the subject 126.

Figure 5:
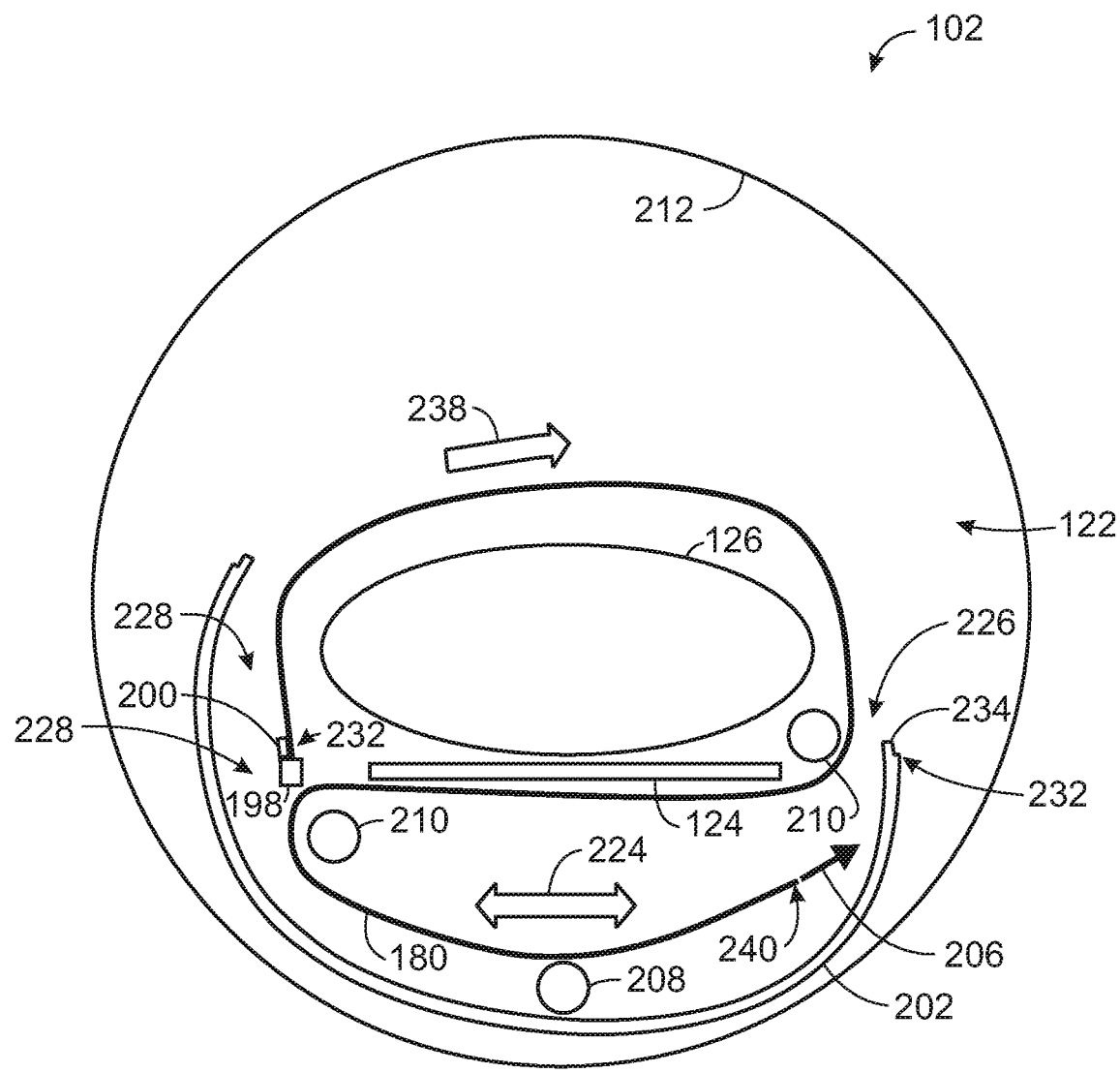
FIG. 5 illustrates the flexible RF receiving coil array in FIG. 3 disposed and secured about the subject (e.g., in a deployed position), in accordance with aspects of the present disclosure.

FIG. 5 illustrates the flexible RF receiving coil array 180 in FIG. 3 disposed and secured about the subject 126 (e.g., in a deployed position). The curved arm 202 continues rotating in the direction 236 (shown in FIG. 4) until the one or more fasteners 192 (see FIG. 3) on the end 230 of the flexible RF receiving coil array 180 are engaged with and secured by the one or more corresponding receptacles 198 on the second side 228. Upon securing the end 230 of the flexible RF receiving coil array 180 to the second side 228, the curved arm 202 reverses direction as indicated by arrow 238 until the one or more hooks or protrusion 234 on the end 232 of the curved arm 202 disengage from the one or more corresponding connectors on the end 230 of flexible RF receiving coil array 180. The curved arm 202 (via the drive mechanism) rotates to the position seen in FIG. 3. A longitudinal length of the flexible RF receiving coil array 180 is at least equal to a circumference of a largest subject 126 that can be scanned within the bore 122 of the MRI scanner 102. As depicted in FIG. 5, the set of rollers 210 keep an excess portion of the flexible RF receiving coil array 180 not disposed over the subject 126 during the scan in the rolled or folded arrangement underneath the table 124.

As depicted in FIG. 5, a tension spring 206 (e.g., pull spring) is coupled to an end 240 (opposite the end 232) of the flexible RF receiving coil array 180. The tension spring 206 provide tension to keep the flexible RF receiving coil array 180 secure (e.g., disposed along the contours) about the subject 126. Upon release or unfastening of the flexible RF receiving coil array 180 from the second side 228, the tension spring 206 facilitates (via a force it exerts) the return of the flexible RF receiving coil array 180 to underneath the table 124 (e.g., to the stored position).

It should be noted that instead of a clockwise orientation for deploying the flexible RF receiving coil array 180 and a counter-clockwise orientation for returning the flexible, RF receiving coil array 180 from the end view depicted in FIGS. 3-5, the flexible RF receiving coil array 180 and the automated deployment system 184 may be configured to operate in the opposite manner in reference to the same end view.

Figure 6:
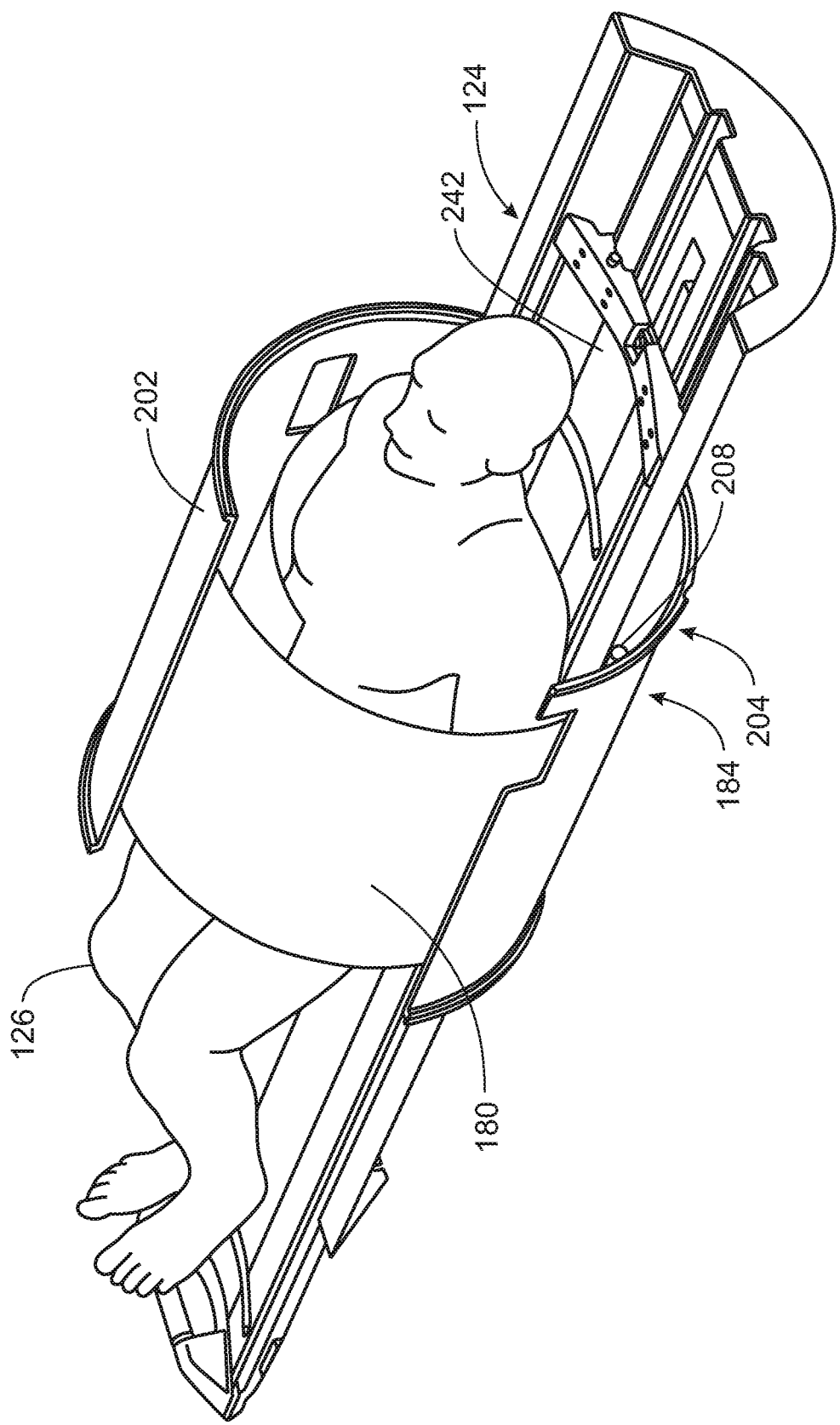
FIG. 6 illustrates a perspective view of a flexible RF receiving coil array being deployed about the subject utilizing a curved arm, in accordance with aspects of the present disclosure.

FIG. 6 illustrates a perspective view of the flexible RF receiving coil array 180 being deployed about the subject 126 utilizing the curved arm 202. As depicted, the subject 126 is disposed on a cradle 242 of the table 124. Some components of the automated deployment system 184 (e.g., rollers, tension spring, etc.) are not shown. As depicted, the curved arm 202 is coupled to the drive mechanism 208. As described above, the drive mechanism 208 is configured to rotate the curved arm 202 to pull the flexible RF receiving coil array 180 about the subject 126 (e.g., utilizing the features (hooks, protrusions, connectors, etc.) on the flexible RF receiving coil array 180 and the curved arm 202.

Figure 7:
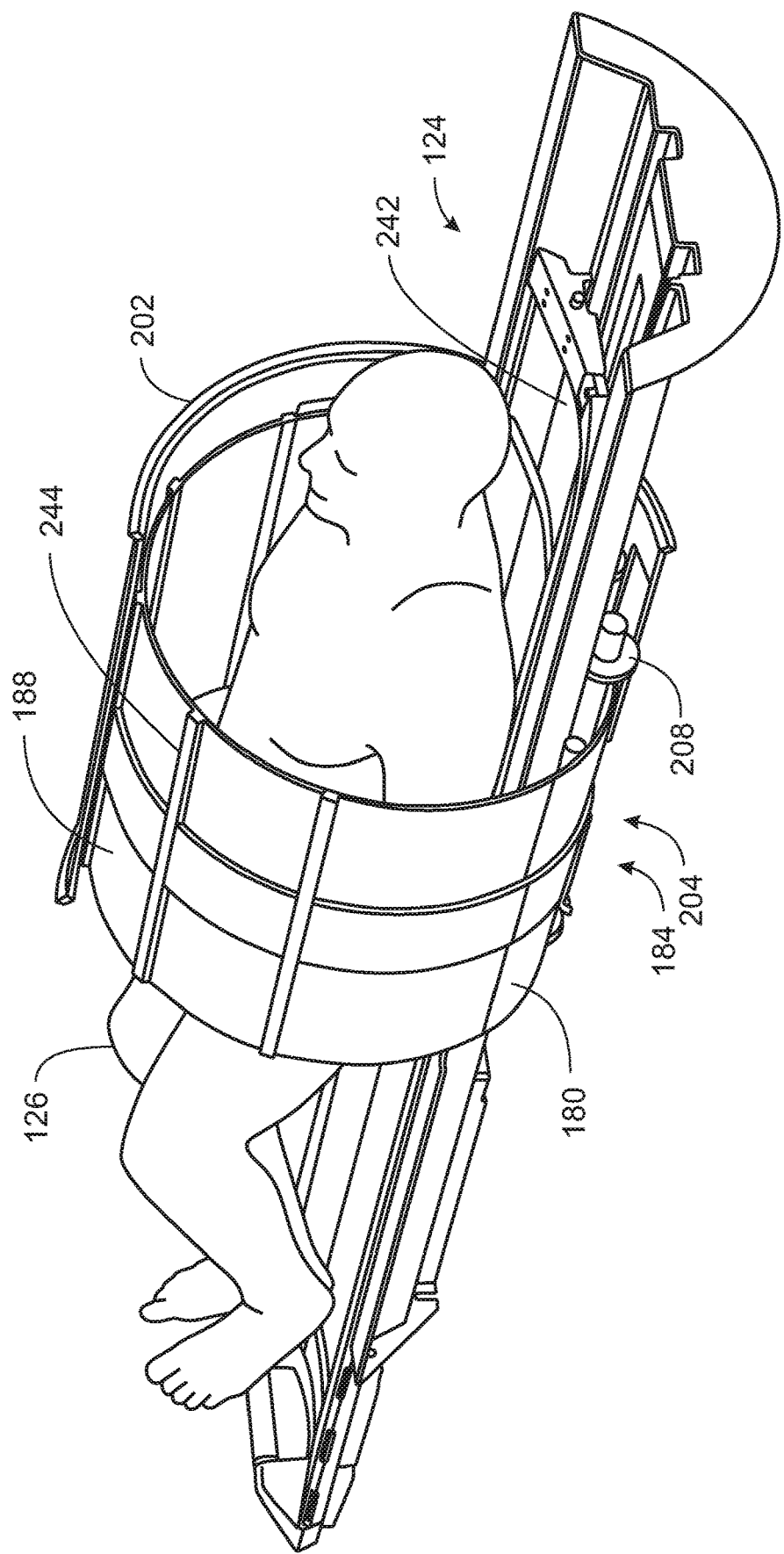
FIG. 7 illustrates a perspective view of a flexible RF receiving coil array being deployed about the subject utilizing a curved arm (e.g., having external antenna on the flexible RF receiving coil array), in accordance with aspects of the present disclosure.

As mentioned above, in certain embodiments, the flexible RF receiving coil array 180 includes an antenna (e.g., internally) coupled to the RF coil 185 and configured to wirelessly receive and transmits signals. In certain embodiments, the antenna 187 may be disposed external to the flexible RF receiving coil array 180. FIG. 7 illustrates a perspective view of the flexible RF receiving coil array 180 being deployed about the subject 126 utilizing the curved arm 202 (e.g., having external antenna on the flexible RF receiving coil array 180). The flexible RF receiving coil array 180 is as described in FIG. 6. As depicted, an external antenna 244 is disposed on an outer surface of the flexible enclosure 188 of the flexible RF receiving coil array 180. The external antenna 244 is configured to wirelessly receive (e.g., control signals) and transmit signals (e.g., having scan data) to circuitry of the MRI scanner.

Figure 8:
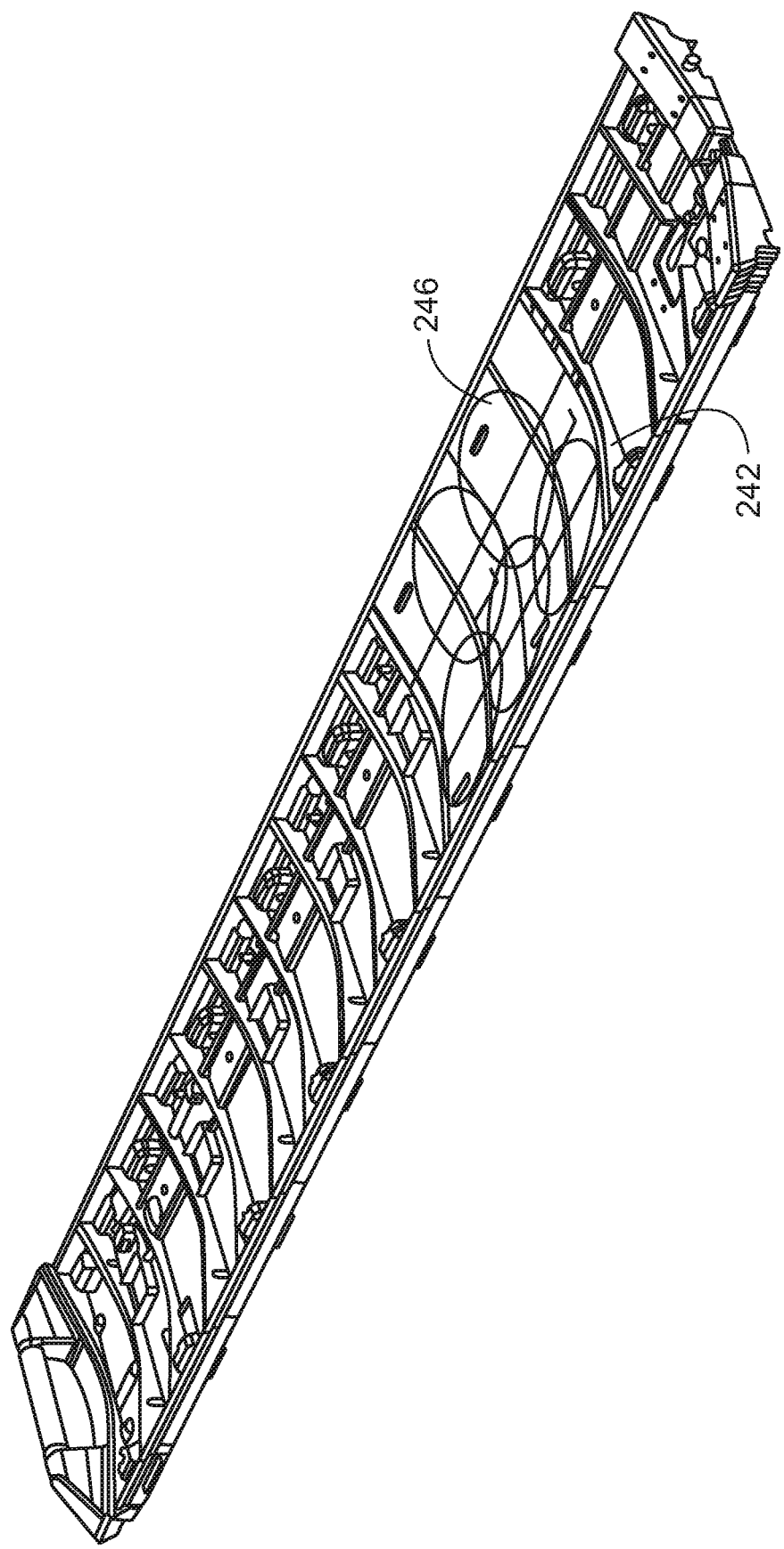
FIG. 8 illustrates a perspective view of a cradle having an antenna, in accordance with aspects of the present disclosure.

In certain embodiments, the antenna may be separate from the flexible RF receiving coil array. FIG. 8 illustrates a perspective view of the cradle 242 having an antenna 246. The antenna 246 is disposed internally with the cradle 242.

The cradle 242 may include a side connection that when the cradle 242 as part of the table is disposed within the bore of the MRI scanner couple to the flexible RF receiving coil array 180 to enable wireless receiving and transmitting of signals to circuitry of the MRI scanner.

FIG. 9 illustrates a linear arrangement of the channels 186 of the flexible RF receiving coil array 180. The flexible RF receiving coil array 180 includes the RF coil 185 having the plurality of channels 186 (e.g., elements or loops) disposed within the flexible enclosure 188. As depicted, the RF coil 185 has 16 channels 186. In certain embodiments, the number of channels 186 may be different (e.g., 8, 32, 64 or any other number of channels 186). The plurality of channels 186 is arranged in a plurality of rows 248 along a longitudinal length 250 of the flexible RF receiving coil array 180. As depicted, the plurality of channels 186 is arranged in two rows 248 (rows 252 and 254). In certain embodiments, the plurality of channels 186 may be arranged in more than two rows 248. As depicted, the plurality of rows 248 is aligned along a field of view (FOV) 256. Each channel 186 of the plurality of channels 186 is located within the FOV 256 and is utilized during a scan. In certain embodiments, the plurality of channels 186 is staggered with respect to each other along a longitudinal length (or a longitudinal axis) of the flexible RF receiving coil array 180.

FIG. 10 illustrates a staggered arrangement of the channels 186 of the flexible RF receiving coil array 180. The flexible RF receiving coil array 180 includes the RF coil 185 having the plurality of channels 186 (e.g., elements or loops) disposed within the flexible enclosure 188. As depicted, the RF coil 185 has 16 channels 186. In certain embodiments, the number of channels 186 may be different (e.g., 8, 32, 64 or any other number of channels 186). The plurality of channels 186 is arranged in the plurality of rows 248 along the longitudinal length 250 of the flexible RF receiving coil array 180. As depicted, the plurality of channels 186 is arranged in two rows 248 (rows 252 and 254). In certain embodiments, the plurality of channels 186 may be arranged in more than two rows 248. As depicted, the plurality of channels 186 is staggered with respect to each other along the longitudinal length 250 (or a longitudinal axis) of the flexible RF receiving coil array 180. For example, the row 252 is staggered relative to the row 254. Each channel 186 of the plurality of channels 186 is located within the FOV 256 and is utilized during a scan. Whether the channels 186 are in a linear arrangement or a staggered arrangement, the flexible RF receiving coil array 180, the impact on signal-to-noise ratio for the flexible RF receiving coil array 180 is minimal compared to traditional RF receiving coil sets.

Figure 11A:
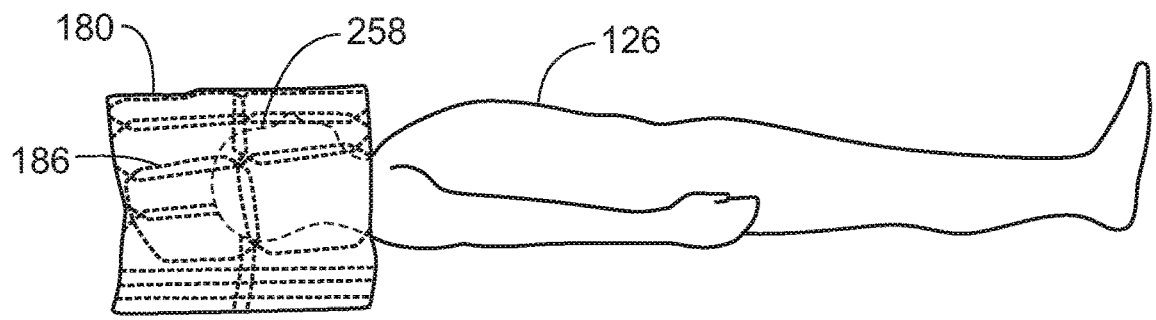
FIGS. 11A-11C illustrate different schematic views of a flexible RF receiving coil array disposed about a head of a subject, in accordance with aspects of the present disclosure.
Figure 11B:
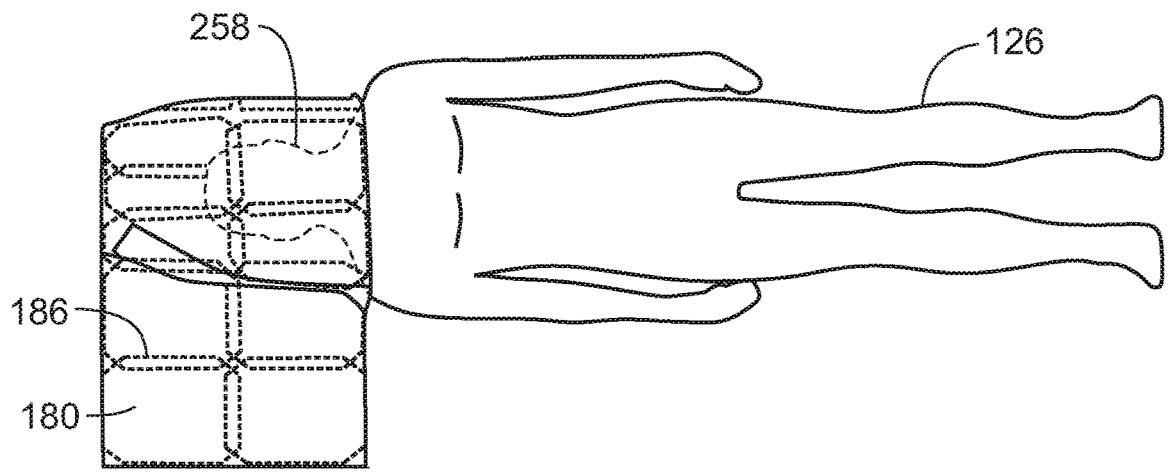
Figure 11C:
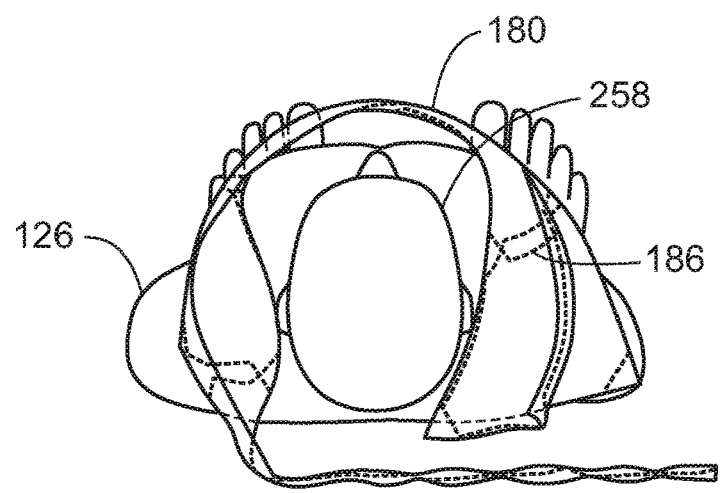

As noted above, the flexible RF receiving coil array 180 is configured to be utilized for scanning all parts of the anatomy of the subject 126 (e.g., patient). FIGS. 11A-11C illustrate different schematic views of the flexible RF receiving coil array 180 disposed about a head 258 of the subject 126. FIG. 11A is a side view of the flexible RF receiving coil array 180 disposed about the head 258 of the subject 126. FIG. 11B is a top view of the flexible RF receiving coil array 180 disposed about the head 258 of the subject 126. FIG. 11C is an end view (e.g., from the end of the subject with the head 258) of the flexible RF receiving coil array 180 disposed about the head 258 of the subject 126. Although not shown in FIGS. 11A-11C, the flexible RF receiving coil array 180 may be wrapped around a supporting dome on the top of the head 258. As depicted, the flexible RF receiving coil array 180 is completely wrapped around the head 258.

As depicted, each channel 186 of the flexible RF receiving coil array 180 is located within the FOV and is utilized during a scan.

Figure 12A:
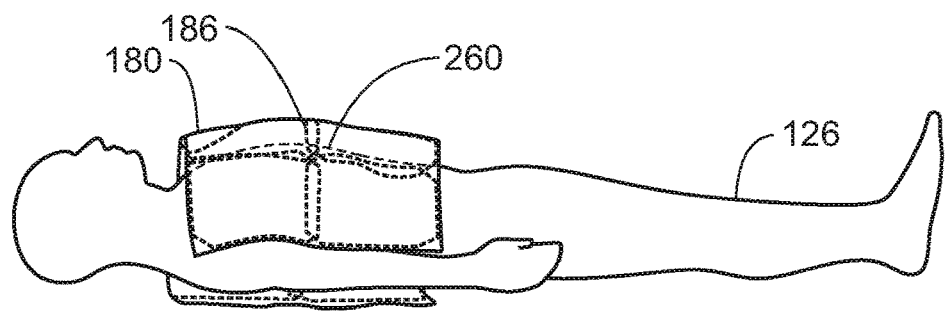
FIGS. 12A-12C illustrate different schematic views of a flexible RF receiving coil array disposed about a torso of a subject, in accordance with aspects of the present disclosure.
Figure 12B:
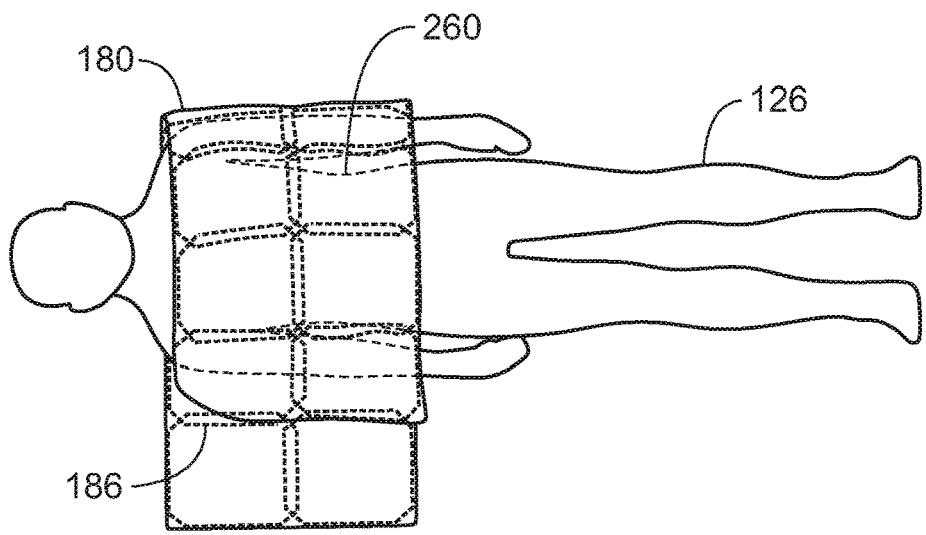
Figure 12C:
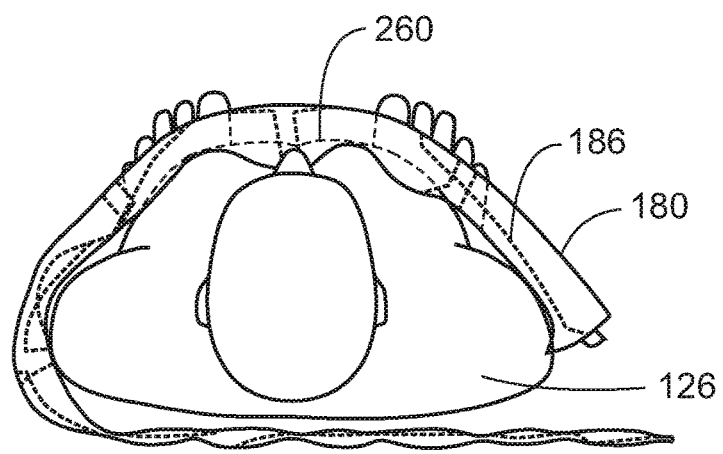

FIGS. 12A-12C illustrate different schematic views of the flexible RF receiving coil array 180 disposed about a torso 260 of the subject 126. FIG. 12A is a side view of the flexible RF receiving coil array 180 disposed about the torso 260 of the subject 126. FIG. 12B is a top view of the flexible RF receiving coil array 180 disposed about the torso 260 of the subject 126. FIG. 12C is an end view (e.g., from the end of the subject with the head) of the flexible RF receiving coil array 180 disposed about the torso 260 of the subject 126. As depicted, the flexible RF receiving coil array 180 is completely wrapped around the torso 260. As depicted, each channel 186 of the flexible RF receiving coil array 180 is located within the FOV and is utilized during a scan.

Figure 13A:
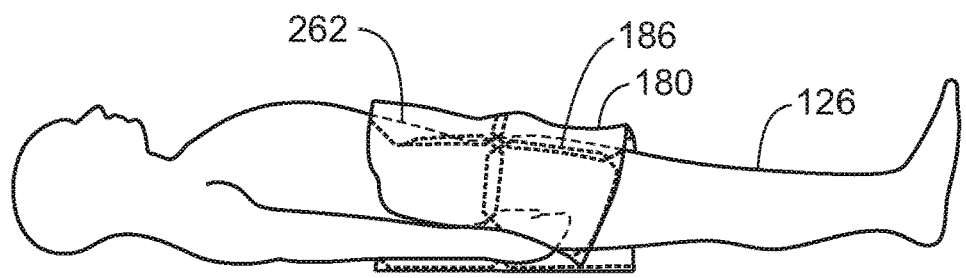
FIGS. 13A-13C illustrate different schematic views of a flexible RF receiving coil array disposed about a pelvis of a subject, in accordance with aspects of the present disclosure.
Figure 13B:
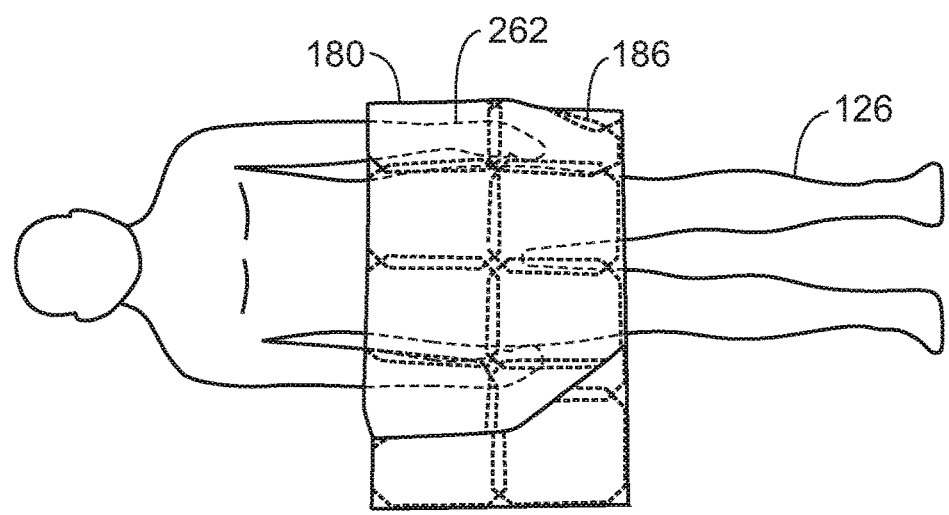
Figure 13C:
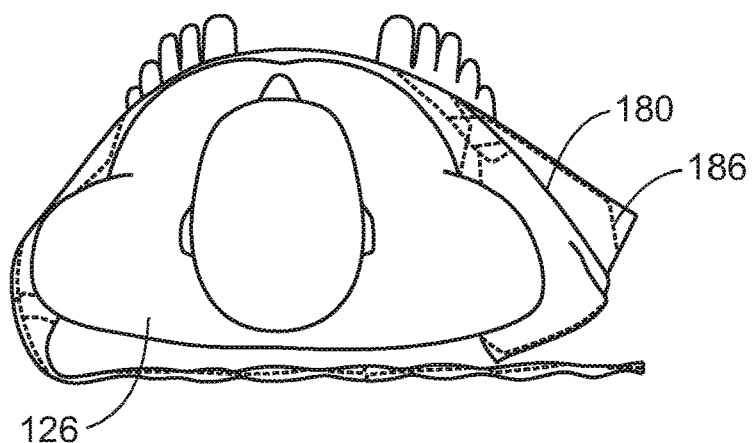

FIGS. 13A-13C illustrate different schematic views of the flexible RF receiving coil array 180 disposed about a pelvis 262 of the subject 126. FIG. 13A is a side view of the flexible RF receiving coil array 180 disposed about the pelvis 262 of the subject 126. FIG. 13B is a top view of the flexible RF receiving coil array 180 disposed about the pelvis 262 of the subject 126. FIG. 13C is an end view (e.g., from the end of the subject with the head) of the flexible RF receiving coil array 180 disposed about the pelvis 262 of the subject 126. As depicted, the flexible RF receiving coil array 180 is completely wrapped around the pelvis 262. As depicted, each channel 186 of the flexible RF receiving coil array 180 is located within the FOV and is utilized during a scan.

Figure 14A:
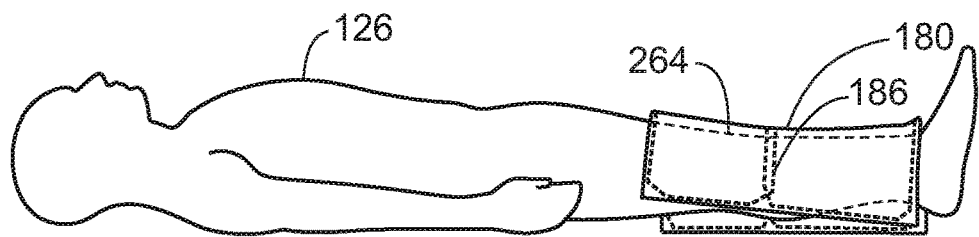
FIGS. 14A-14C illustrate different schematic views of a flexible RF receiving coil array disposed about legs of a subject, in accordance with aspects of the present disclosure.
Figure 14B:
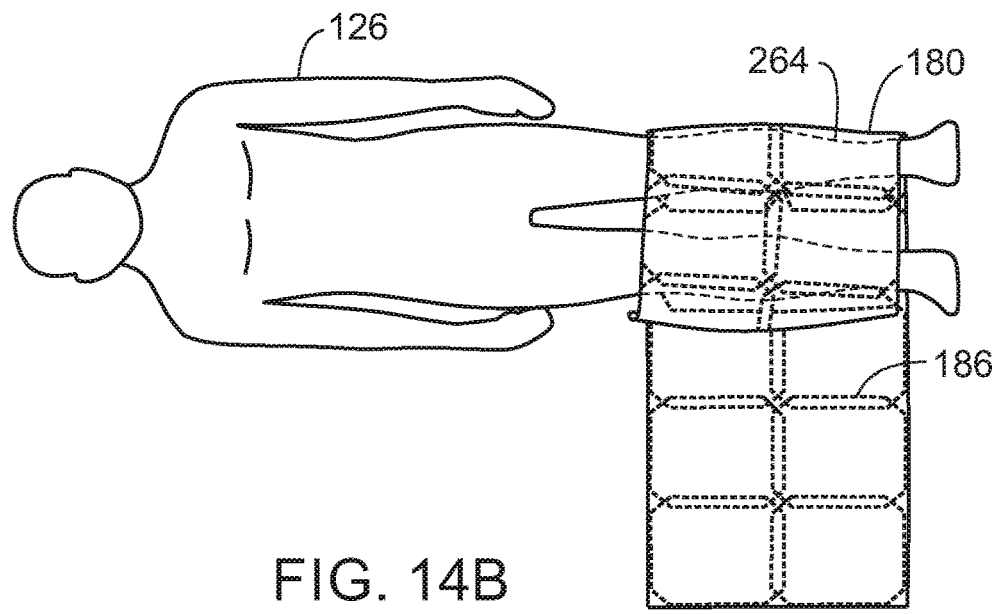
Figure 14C:
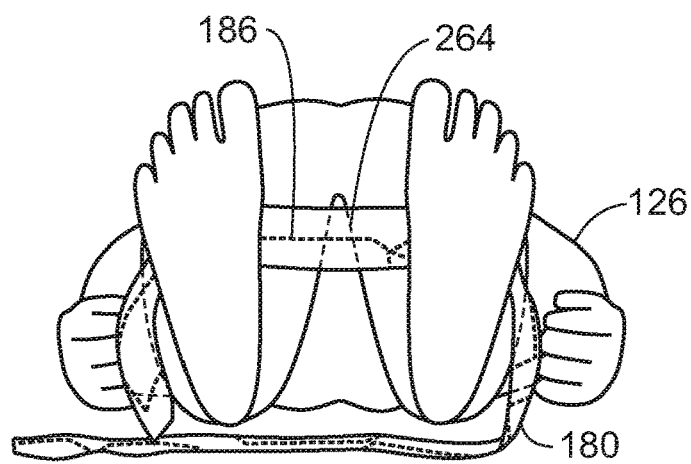

FIGS. 14A-14C illustrate different schematic views of the flexible RF receiving coil array 180 disposed about legs 264 of the subject 126. FIG. 14A is a side view of the flexible RF receiving coil array 180 disposed about the legs 264 of the subject 126. FIG. 14B is a top view of the flexible RF receiving coil array 180 disposed about the legs 264 of the subject 126. FIG. 14C is an end view (e.g., from the end of the subject with the legs 264) of the flexible RF receiving coil array 180 disposed about the legs 264 of the subject 126. As depicted, the flexible RF receiving coil array 180 is completely wrapped around the legs 264. As depicted, each channel 186 of the flexible RF receiving coil array 180 is located within the FOV and is utilized during a scan.

Figure 15:
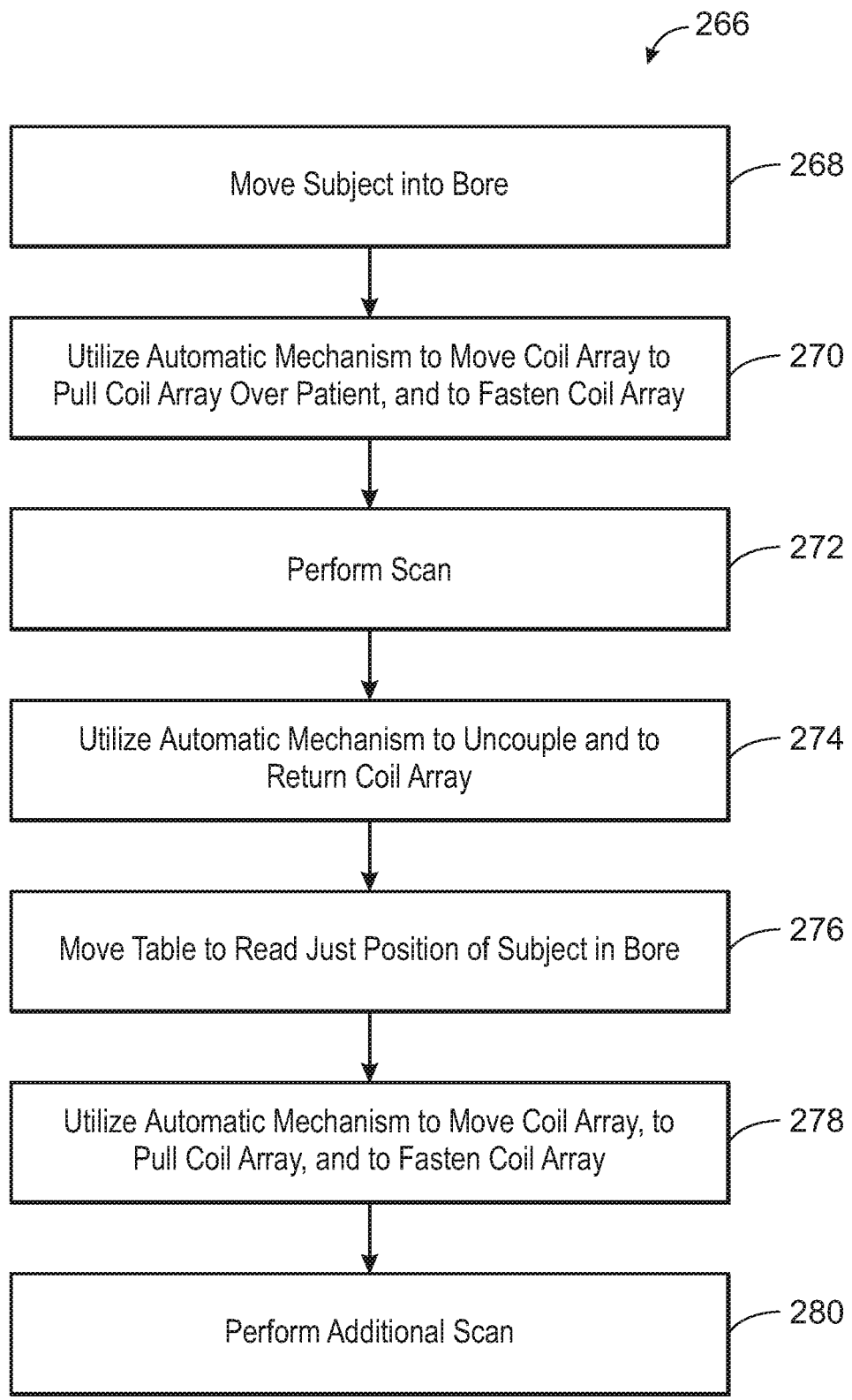
FIG. 15 illustrates a flow chart of a method for performing an MRI scan, in accordance with aspects of the present disclosure.

FIG. 15 illustrates a flow chart of a method 266 for performing an MRI scan. One or more steps of the method 266 may be performed by components (e.g., control circuitry) of the magnetic resonance imaging system 100 in FIG. 1. One or more of the steps of the method 266 may be performed simultaneously or in a different order from the order depicted in FIG. 15.

The method 266 includes moving a subject into a bore of an MRI scanner (e.g., MRI scanner 102 in FIG. 1) via a table (block 268). The method 266 also includes utilizing an automated mechanism to automatically move a flexible radio frequency (RF) receiving coil array (e.g., flexible RF receiving coil array 180 in FIG. 2) from underneath the table on a first side of the subject, to pull the flexible RF receiving coil array over the subject from the first side to a second side of the subject opposite the first side, and to fasten the flexible RF receiving coil array on the second side in preparation for a scan with the MRI scanner (block 270). As described above, the flexible RF receiving coil array is integrated within the bore and electronically coupled directly to the MRI scanner, the flexible RF receiving coil array remains in the bore regardless of a position of the table, and the flexible RF receiving coil array is located underneath the table when the table is located within the bore. The method 266 further includes performing a scan (via the MRI scanner) of a portion (e.g., head, torso, pelvis, legs) of the anatomy of the subject that the flexible RF receiving coil array is disposed about (e.g., wrapped around) (block 272).

The method 266 even further includes, after the scan of the subject, utilizing the automated mechanism to automatically uncouple the flexible RF receiving coil array and to return the flexible RF receiving coil array to underneath the table (block 274). The method 266 still further includes, after return of the flexible RF receiving coil array to underneath the table, moving the table to readjust a position of the subject within the bore (block 276). The method 266 yet further includes utilizing the automated mechanism to automatically move the flexible RF receiving coil array from underneath the table on the first side of the subject, to pull the flexible RF receiving coil array over the subject from the first side to the second side of the subject opposite the first side, and to fasten the flexible RF receiving coil array on the second side in preparation for an additional scan with the MRI scanner, wherein the additional scan is for a different portion of the anatomy of the subject (block 278). The method 266 also includes performing the additional scan (via the MRI scanner) of a different portion (e.g., head, torso, pelvis, legs) of the anatomy of the subject (than scanned in the first scan) that the flexible RF receiving coil array is disposed about (e.g., wrapped around) (block 280).

Figure 16:
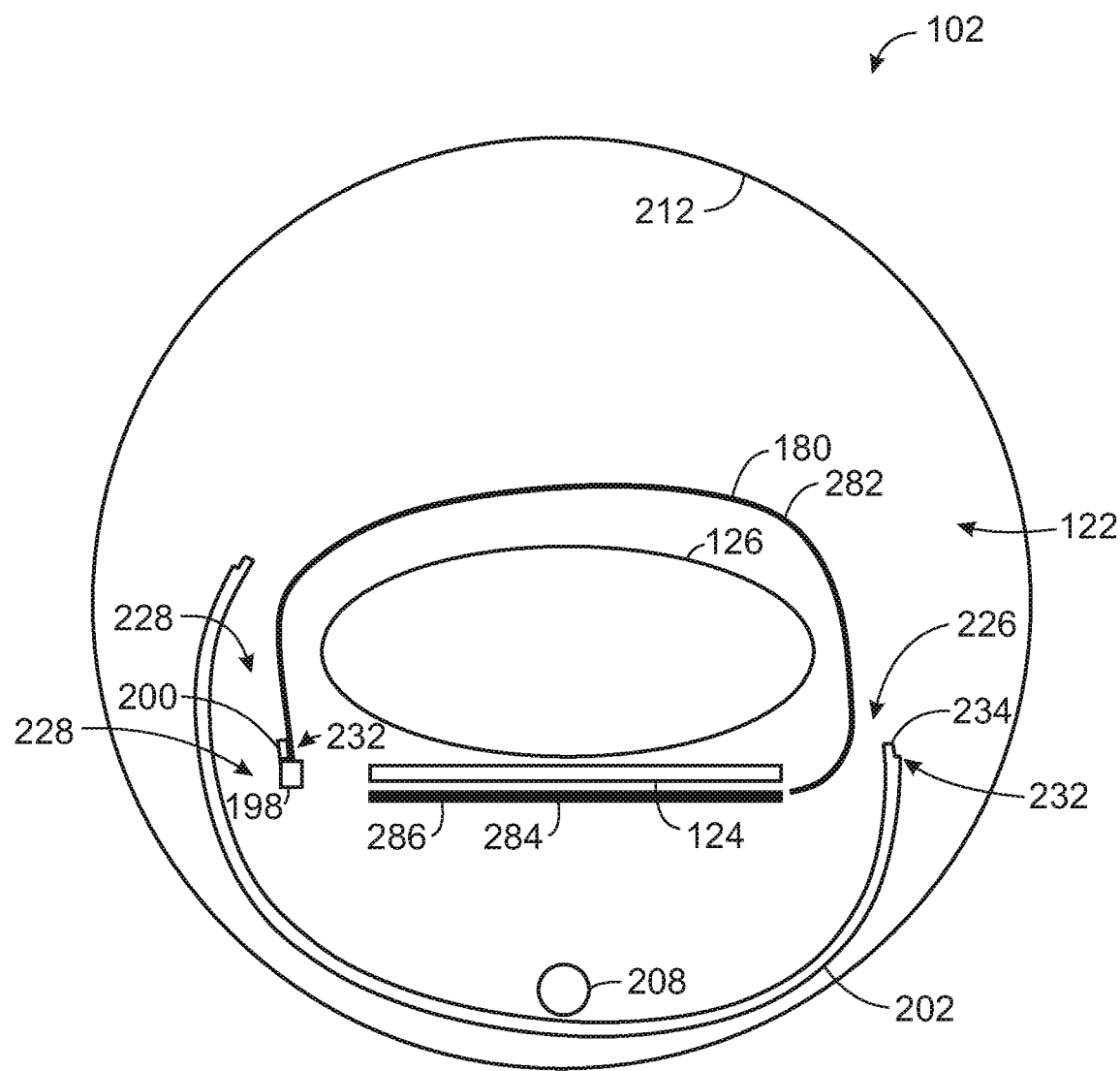
FIG. 16 illustrates a flexible RF receiving coil array (e.g., anterior array) disposed and secured about the subject (e.g., in a deployed position) with an RF receiving coil array (e.g., posterior array) disposed under a table, in accordance with aspects of the present disclosure.

FIG. 16 illustrates the flexible RF receiving coil array 180 (e.g., anterior array 282) disposed and secured about the subject 126 (e.g., in a deployed position) with an RF receiving coil array 284 (e.g., posterior array 286) disposed under the table 124. The flexible RF receiving coil array 180 is similarly disposed about the subject 126 utilizing the curved arm 202 as described above. However, instead of having a portion of the flexible RF receiving coil array 180 folded underneath the table 124 when deployed, the flexible RF receiving coil array 180 is utilized as the anterior array 282 while an RF receiving coil array 284 is utilized as a permanent posterior array 286. The RF receiving coil array 284 is located in a position underneath the table 124 when the table is disposed within the bore 122. Similar to the flexible RF receiving coil array 180, the RF receiving coil array 284 remains in the bore 122 regardless of the position of the table 124 that moves the subject 126 (e.g., patient or object) into and out of the bore 122. In particular, the flexible RF receiving coil array 284 is not coupled to the table (regardless of the position of the table 124). The flexible RF receiving coil array 180 and the RF receiving coil array 284 are utilized together during a scan. This embodiment enables a more compact arrangement.

Technical effects of the disclosed subject matter include eliminating the need for any connectors or cables for use with RF receiving coils in the table utilized for an MRI scan. Thus, the table can be utilized purely as a mechanical support. Technical effects of the disclosed subject matter also include eliminating the need for coil placement and adjustment by a medical technician. Technical effects of the disclosed subject matter further include enabling all existing channels to be in the field of view and to be utilized during a scan. Technical effects of the disclosed subject matter even further include providing for a flexible RF receiving coil array that can be utilized for scanning all parts of the anatomy. This may increase or speed up workflow. This may also reduce costs associated with medial professional assistance. This may also reduce costs since a scanner does not need to be equipped with multiple types of RF receiving coils.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

This written description uses examples to disclose the present subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A magnetic resonance imaging (MRI) system, comprising:
   an MRI scanner having a bore;
   a table configured to move a subject to be imaged into and out of the bore of the MRI scanner;
   a flexible radio frequency (RF) receiving coil array permanently coupled to and disposed within the bore and electronically coupled directly to the MRI scanner, wherein the flexible RF receiving coil array remains in the bore regardless of a position of the table, and the flexible RF receiving coil array within the bore is located underneath the table when the table is initially moved into the bore; and
   an automated mechanism configured to automatically move the flexible RF receiving coil array from underneath the table on a first side of the subject, to pull the flexible RF receiving coil array over the subject from the first side to a second side of the subject opposite the first side, and to fasten the flexible RF receiving coil array on the second side in preparation for a scan with the MRI scanner, wherein the automated mechanism comprises a set of rollers located in the bore that is configured to keep the flexible RF receiving coil array in a rolled or folded arrangement in a stored position within the bore prior to being pulled over the subject.

2. The MRI imaging system of claim 1, wherein the flexible RF receiving coil array is not coupled to the table regardless of the position of the table.

3. The MRI imaging system of claim 1, wherein the automated mechanism is configured, after the scan of the subject, to automatically uncouple the flexible RF receiving coil array and to return the flexible RF receiving coil array to underneath the table.

4. The MRI imaging system of claim 3, wherein the automated mechanism comprises a tension spring to return the flexible RF receiving coil array to underneath the table.

5. The MRI imaging system of claim 1, wherein the automated mechanism comprises a curved arm coupled to a drive mechanism, wherein the curved arm is configured to couple to the flexible RF receiving coil array, and the drive mechanism is configured to rotate the curved arm to pull the flexible RF receiving coil array about the subject.

6. The MRI imaging system of claim 1, wherein the set of rollers is configured to keep an excess portion of the flexible RF receiving coil array not disposed over the subject during the scan in the rolled or folded arrangement underneath the table.

7. The MRI imaging system of claim 1, wherein the flexible RF receiving coil array comprises a plurality of channels, and each channel of the plurality of channels is located within a field of view of the MRI scanner and is utilized during the scan.

8. The MRI imaging system of claim 7, wherein the plurality of channels is arranged in a plurality of rows along a longitudinal length of the flexible RF receiving coil array.

9. The MRI imaging system of claim 8, wherein the plurality of rows is aligned in along the field of view.

10. The MRI imaging system of claim 8, wherein the plurality of rows is staggered with respect to each other along the longitudinal length.

11. The MRI imaging system of claim 1, wherein the flexible RF receiving coil array is configured to be completely wrapped around any anatomical portion of the subject.

12. The MRI imaging system of claim 1, wherein a longitudinal length of the flexible RF receiving coil array is at least equal to a circumference of a largest subject that can be scanned within the bore of the MRI scanner.

13. A method for performing a magnetic resonance imaging (MRI) scan, comprising:
    moving a subject into a bore of an MRI scanner via a table; and
    utilizing an automated mechanism to automatically move a flexible radio frequency (RF) receiving coil array from underneath the table on a first side of the subject, to pull the flexible RF receiving coil array over the subject from the first side to a second side of the subject opposite the first side, and to fasten the flexible RF receiving coil array on the second side in preparation for a scan with the MRI scanner, wherein the flexible RF receiving coil array is permanently coupled to and disposed within the bore and electronically coupled directly to the MRI scanner, the flexible RF receiving coil array remains in the bore regardless of a position of the table, and the flexible RF receiving coil array within the bore is located underneath the table when the table is initially moved into the bore, and wherein the automated mechanism comprises a set of rollers located in the bore that is configured to keep the flexible RF receiving coil array in a rolled or folded arrangement in a stored position within the bore prior to being pulled over the subject.

14. The method of claim 13, further comprising, after the scan of the subject, utilizing the automated mechanism to automatically uncouple the flexible RF receiving coil array and to return the flexible RF receiving coil array to underneath the table.

15. The method of claim 14, further comprising, after return of the flexible RF receiving coil array to underneath the table:
    moving the table to readjust a position of the subject within the bore; and
    utilizing the automated mechanism to automatically move the flexible RF receiving coil array from underneath the table on the first side of the subject, to pull the flexible RF receiving coil array over the subject from the first side to the second side of the subject opposite the first side, and to fasten the flexible RF receiving coil array on the second side in preparation for an additional scan with the MRI scanner, wherein the additional scan is for a different portion of anatomy of the subject than scanned in the scan.

16. The method of claim 13, wherein the flexible RF receiving coil array is not coupled to the table regardless of the position of the table.

17. The method of claim 13, wherein the flexible RF receiving coil array comprises a plurality of channels, and each channel of the plurality of channels is located within a field of view of the MRI scanner and is utilized during the scan.

18. The method of claim 17, wherein the plurality of channels is arranged in a plurality of rows along a longitudinal length of the flexible RF receiving coil array.

19. The method of claim 13, wherein the automated mechanism comprises a curved arm coupled to a drive mechanism, wherein the curved arm is configured to couple to the flexible RF receiving coil array, and the drive mechanism is configured to rotate the curved arm to pull the flexible RF receiving coil array about the subject.

20. A magnetic resonance imaging (MRI) system, comprising:
an MRI scanner having a bore;
a table configured to move a subject to be imaged into and out of the bore of the MRI scanner;
a flexible radio frequency (RF) receiving coil array permanently coupled to and disposed within the bore and electronically coupled directly to the MRI scanner, wherein the flexible RF receiving coil array is configured to be completely wrapped around any anatomical portion of the subject, the flexible RF receiving coil array remains in the bore regardless of a position of the table, and the flexible RF receiving coil array within the bore is located underneath the table when the table is initially moved into the bore; and
an automated mechanism configured to automatically move the flexible RF receiving coil array from underneath the table on a first side of the subject, to pull the flexible RF receiving coil array over the subject from the first side to a second side of the subject opposite the first side, and to fasten the flexible RF receiving coil array on the second side in preparation for a scan with the MRI scanner, wherein the automated mechanism comprises a set of rollers located in the bore that is configured to keep the flexible RF receiving coil array in a rolled or folded arrangement in a stored position within the bore prior to being pulled over the subject; and
wherein the flexible RF receiving coil array comprises a plurality of channels, each channel of the plurality of channels is located within a field of view of the MRI scanner and is utilized during the scan, and the plurality of channels is arranged in a plurality of rows along a longitudinal length of the flexible RF receiving coil array.

* * * * *